(12) United States Patent
Sano et al.

(10) Patent No.: US 10,335,109 B2
(45) Date of Patent: Jul. 2, 2019

(54) RADIATION PHASE-CONTRAST IMAGING DEVICE

(71) Applicant: Shimadzu Corporation, Kyoto (JP)

(72) Inventors: Satoshi Sano, Kyoto (JP); Toshiyuki Sato, Kyoto (JP); Koichi Tanabe, Kyoto (JP); Shingo Furui, Kyoto (JP); Toshinori Yoshimuta, Kyoto (JP); Hiroyuki Kishihara, Kyoto (JP); Takahiro Doki, Kyoto (JP); Akira Horiba, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 161 days.

(21) Appl. No.: 15/555,663

(22) PCT Filed: Mar. 6, 2015

(86) PCT No.: PCT/JP2015/056747
§ 371 (c)(1),
(2) Date: Sep. 5, 2017

(87) PCT Pub. No.: WO2016/143015
PCT Pub. Date: Sep. 15, 2016

(65) Prior Publication Data
US 2018/0042571 A1 Feb. 15, 2018

(51) Int. Cl.
*A61B 6/00* (2006.01)
*G01N 23/04* (2018.01)
*G01N 23/20* (2018.01)

(52) U.S. Cl.
CPC .......... *A61B 6/5258* (2013.01); *A61B 6/4035* (2013.01); *A61B 6/484* (2013.01); *A61B 6/487* (2013.01); *G01N 23/043* (2013.01); *G01N 23/20075* (2013.01)

(58) Field of Classification Search
CPC ....... A61B 6/4035; A61B 6/484; A61B 6/487; A61B 6/5258; G01N 23/043; G01N 23/20075
See application file for complete search history.

(56) References Cited

U.S. PATENT DOCUMENTS

2013/0181130 A1   7/2013   Itoh et al.

FOREIGN PATENT DOCUMENTS

| JP | 2012-16370 A | 1/2012 |
| JP | 2012-108098 A | 6/2012 |

OTHER PUBLICATIONS

International Search Report with English translation and Written Opinion dated Apr. 28, 2015 of corresponding International application No. PCT/JP2015/056747; 8 pgs.

*Primary Examiner* — Mark R Gaworecki
(74) *Attorney, Agent, or Firm* — Maier & Maier, PLLC

(57) ABSTRACT

Provided is a radiation phase difference imaging apparatus in which a separation distance between a phase grating and a radiation detector is optimized. The separation distance between the phase grating and a detection surface of an FPD is determined based on the magnitude of noise corruption in a self-image projected onto the detection surface. The magnitude of the effect of the noise is used as a basis for assessing the separation distance. It is determined whether a distance Zd is appropriate for imaging, based on the magnitude of noise corruption in the self-image in a self-image picture which is obtained when the distance Zd is the distance between the phase grating and the detection surface of the FPD. The separation distance can thus be optimized based on actual conditions of an actual X-ray source that emits a plurality of types of X-rays.

5 Claims, 5 Drawing Sheets (A)          (B)

SELF-IMAGE

RADIATION PHASE-CONTRAST IMAGING DEVICE

TECHNICAL FIELD

The present invention relates to a radiation phase difference imaging apparatus capable of imaging an inner structure of an object by using a phase difference of a radiation transmitted through the object.

BACKGROUND ART

Hitherto, there are known radiation imaging apparatuses which image an inner structure of an object by transmitting a radiation through the object. In a general radiation imaging apparatus among these apparatuses, a radiation is radiated to an object to be transmitted through the object and a projected image of the radiation is imaged. In such a projected image, shading appears depending on the ease of the transmission of the radiation and this shading indicates an inner structure of the object.

In such a radiation imaging apparatus, only an object having a property of absorbing a radiation to some extent can be imaged. For example, a soft tissue of a living body hardly absorbs a radiation. Even when such a tissue is imaged by a general apparatus, almost nothing appears on the projected image. In this way, there is a limit in principle of the general radiation imaging apparatus at the time of imaging the inner structure of the object which hardly absorbs the radiation.

Here, a radiation phase difference imaging apparatus which images the inner structure of the object by using the phase difference of the transmitted radiation can be considered. Such an apparatus images the inner structure of the object by using Talbot interference.

The Talbot interference will be described. A radiation having the same phase is radiated from a radiation source 53 of FIG. 10. When the radiation passes through a phase grating 55 having a fabric shape, an image of the phase grating 55 appears on a projection surface separated from the phase grating 55 by a predetermined distance (Talbot distance). This image is called a self-image. The self-image is not a simple projected image of the phase grating 55. The self-image is formed only at a position in which the projection surface is separated from the phase grating 55 by the Talbot distance. The self-image is formed by interference fringes caused by light interference. The self-image of the phase grating 55 appears at the Talbot distance because the phases of the radiation generated from the radiation source 53 are aligned. When the phases of the radiation are disturbed, the self-image appearing at the Talbot distance is also disturbed.

The radiation phase difference imaging apparatus images the inner structure of the object by using the disturbance of the self-image. An object is placed between the radiation source and the phase grating 55. Since the object hardly absorbs the radiation, most of the radiation incident to the object is radiated toward the phase grating 55.

The radiation does not completely pass through the object. The phase of the radiation changes while the radiation passes through the object. The radiation radiated from the object passes through the phase grating 55 while the phase is changed. When the radiation is observed on the projection surface positioned at the Talbot distance, the self-image of the phase grating 55 is disturbed. The disturbance degree of the self-image indicates a change in phase of the radiation.

The degree to which the phase of the radiation transmitted through the object specifically changes depends on a position in which the radiation passes through the object. If the object is homogeneous, a change in phase of the radiation might be the same throughout the object. However, the object generally has a certain inner structure. When the radiation is transmitted through such an object, a change in phase is not uniform.

Thus, the inner structure of the object can be understood when a change in phase can be understood. A change in phase can be understood by observing the self-image of the phase grating 55 at the Talbot distance.

The self-image of the phase grating 55 is detected by a radiation detector which is separated from the phase grating 55 by a predetermined distance. The separation distance between the phase grating 55 and the radiation detector may not be set arbitrarily. When the separation distance is not suitable, the self-image is not captured on the radiation detector. The suitable separation distance is determined by the distance from the radiation source 53 to the phase grating 55, the finesse of the fabric shape forming the phase grating 55, and the wavelength of the radiation output from the radiation source 53. Patent Document 1 introduces mathematical expressions relating to these parameters. When the suitable separation distance needs to be obtained, other parameters such as a distance from the radiation source 53 to the phase grating 55 may be applied to a mathematical expression.

CITATION LIST

Patent Document

Patent Document 1: JP-A-2012-16370

SUMMARY OF THE INVENTION

Technical Problem

However, the above-described related art has the following problems.

That is, the apparatus having a conventional configuration is not sufficiently compatible with the actual circumstances ox the radiation source.

It is actually quite difficult to prepare a monochromatic light output type radiation source that outputs only a certain wavelength. Therefore, as a radiation source used in an actual apparatus, there is only one choice to select a radiation source outputting radiations having various wavelengths.

On the assumption that such a radiation source 53 is used, it is considered how to appropriately set the separation distance between the phase grating 55 and the radiation detector. When the distance from the radiation source 53 to the phase grating 55 and the finesse of the fabric shape forming the phase grating 55 are uniform, the suitable separation distance is determined by the wavelength of the radiation. When the wavelength of the radiation radiated from the radiation source 53 is uniform, the suitable separation distance can be easily determined based on the wavelength. However, when the radiation source 53 radiating various wavelengths is used, it is not possible to know the wavelength to be applied to the mathematical expression for obtaining the suitable separation distance.

As one solution, it is considered that the suitable separation distance is obtained based on the wavelength of the radiation having the strongest intensity among the wavelengths of the radiations output from the radiation source 53. However, it is not possible to guarantee that the separation distance determined in this way is really suitable.

The invention has been made in view of such circumstances and an object of the invention is to provide a radiation phase difference imaging apparatus in which a separation distance between a phase grating and a radiation detector is optimized.

Solution to Problem

The invention has the following configuration in order to solve the above-described problems.

That is, a radiation phase difference imaging apparatus according to the invention includes: a radiation source which radiates a plurality of radiations having different wavelengths; a phase grating in which absorbers extending in one direction and absorbing a radiation are arranged in a direction orthogonal to one direction; a detection unit which detects a self-image of the phase grating formed by a Talbot interference on a detection surface detecting a radiation; a self-image picture generation unit which generates a self-image picture capturing a self-image based or an output of the detection unit; and a fluoroscopic image generation unit which generates a fluoroscopic image obtained by imaging a phase difference inside a subject based on the self-image picture, wherein a distance between the phase grating and the detection surface of the detection unit is determined based on how much the self-image captured on the detection surface is disturbed by noise.

[Operation/Effect] According to the invention, it is possible to reliably provide the radiation phase difference imaging apparatus in which the separation distance between the phase grating and the radiation detector is optimized. Certainly, the separation distance between the phase grating and the radiation detector can be obtained as the Talbot distance based on the principle of the Talbot interference. However, the Talbot distance can be uniquely obtained only when the radiation source radiates a single wavelength.

According to the invention, the separation distance between the phase grating and the detection surface of the detection unit is determined based on how much the self-image captured on the detection surface is disturbed by noise. That is, in the configuration of the invention, the noise influence degree is set as an evaluation reference for the separation distance. Then, according to the invention, it is determined whether the distance Zd is suitable for imaging based on how much the self-image on the self-image picture obtained when the distance between the phase grating and the detection surface of the detection unit is set to a certain distance Zd is disturbed by noise. When it is determined that the disturbance of the noise is sufficiently small and the distance Zd is suitable for imaging, the separation distance between the phase grating and the detection surface of the detection unit can be set to the distance Zd. Then, when it is determined that the disturbance of the noise is too large and the distance Zd is not suitable for imaging, the determination on suitability is repeated while changing the separation distance. Likewise, a distance suitable for imaging can be found. In this way, it is possible to optimize the separation distance based on the actual condition of the actual radiation source irradiating a plurality of kinds of radiations.

Further, in the radiation phase difference imaging apparatus, it is more desirable that the distance between the phase grating and the detection unit be determined based on whether the noise influence degree representing how much the self-image picture is influenced by a noise component satisfies a reference for guaranteeing the visibility of the fluoroscopic image.

[Operation/Effect] The above-described configuration more specifically shows the apparatus of the invention. As described above, when the evaluation value called the noise influence degree indicates how much the self-image picture is influenced by the noise component, it is possible to more reliably evaluate the suitability of the distance between the phase grating and the detection surface of the detection unit.

Further, in the radiation phase difference imaging apparatus, it is more desirable that the distance between the phase grating and the detection surface be determined based on the noise influence degree calculated based on the noise intensity indicating the intensity of the noise component appearing on the self-image picture and the contrast of the self-image captured on the self-image picture when the phase grating and the detection surface are separated from each other by a certain distance Zd.

[Operation/Effect] The above-described configuration more specifically shows the apparatus of the invention. When the noise intensity and the contrast of the self-image in a case where the phase grating and the detection surface are separated from each other by a certain distance Zd are calculated and the distance Zd is evaluated as a setting allowed for the imaging of the self-image based on the noise influence degree calculated from these values, it is possible to more reliably evaluate the suitability of the distance between the phase grating and the detection surface of the detection unit.

Further, in the radiation phase difference imaging apparatus, it is more desirable that the noise influence degree be calculated by dividing the contrast by the noise intensity, the distance Zd be a setting allowed for the imaging of the self-image when the noise influence degree is equal to or smaller than a predetermined upper-limit value, and the distance Zd be a setting not allowed for the imaging of the self-image when the noise influence degree is larger than the predetermined upper-limit value.

[Operation/Effect] The above-described configuration more specifically shows the apparatus of the invention. When the noise influence degree is calculated by dividing the contrast by the noise intensity, the noise influence degree is reliably calculated. Further, it is evaluated that the distance Zd is a setting allowed for the imaging of the self-image when the noise influence degree is equal to or smaller than a predetermined upper-limit value. Meanwhile, it is evaluated that the distance Zd is a setting not allowed for the imaging of the self-image when the noise influence degree is larger than the predetermined upper-limit value. Accordingly, it is possible to reliably inhibit the setting of the distance between the phase grating and the detection surface such that the influence of noise strongly appears in the self-image.

Further, in the radiation phase difference imaging apparatus, the contrast and the noise intensity may be calculated based on the measured self-image picture or the simulation.

[Operation/Effect] The above-described configuration more specifically shows the apparatus of the invention. When the intensity calculation unit calculates the contrast and the noise intensity based on the measured self-image picture or the simulation, the noise influence degree can be more reliably calculated.

Advantageous Effects of the Invention

According to the invention, the separation distance between the phase grating and the detection surface of the detection unit is determined based on how much the self-image captured on the detection surface is disturbed by noise. That is, in the configuration of the invention, the noise influence degree is set as an evaluation reference for the separation distance. Then, according to the invention, it is determined whether the distance Zd is suitable for imaging based on how much the self-image on the self-image picture, obtained when the distance between the phase grating and the detection surface of the detection unit is a certain distance Zd, is disturbed by noise. In this way, the separation distance can be optimized based on the setting of the actual radiation source radiating a plurality of kinds of radiations.

MODE FOR CARRYING OUT THE INVENTION

Next, a mode for carrying out the invention will be described by referring to embodiments. An X-ray of the embodiment corresponds to a radiation of the invention. In addition, an FPD of the embodiment is a brief word of a flat panel detector. Since a radiation phase difference imaging apparatus of the invention is also able to image a subject M which does not absorb a radiation much, the apparatus is suitable for fluoroscopy of a substrate in an industrial purpose and is suitable for fluoroscopy of a breast in a medical purpose. It is assumed that a distance between an X-ray source 3 and a phase grating 5 and an arrangement pitch of absorption lines 5a of the phase grating 5 are uniform. Meanwhile, it is assumed that the distance between the phase grating 5 and an FPD 4 can foe adjusted in accordance with the movement of the FPD 4 relative to the phase grating 5.

FIRST EMBODIMENT

Figure 1:
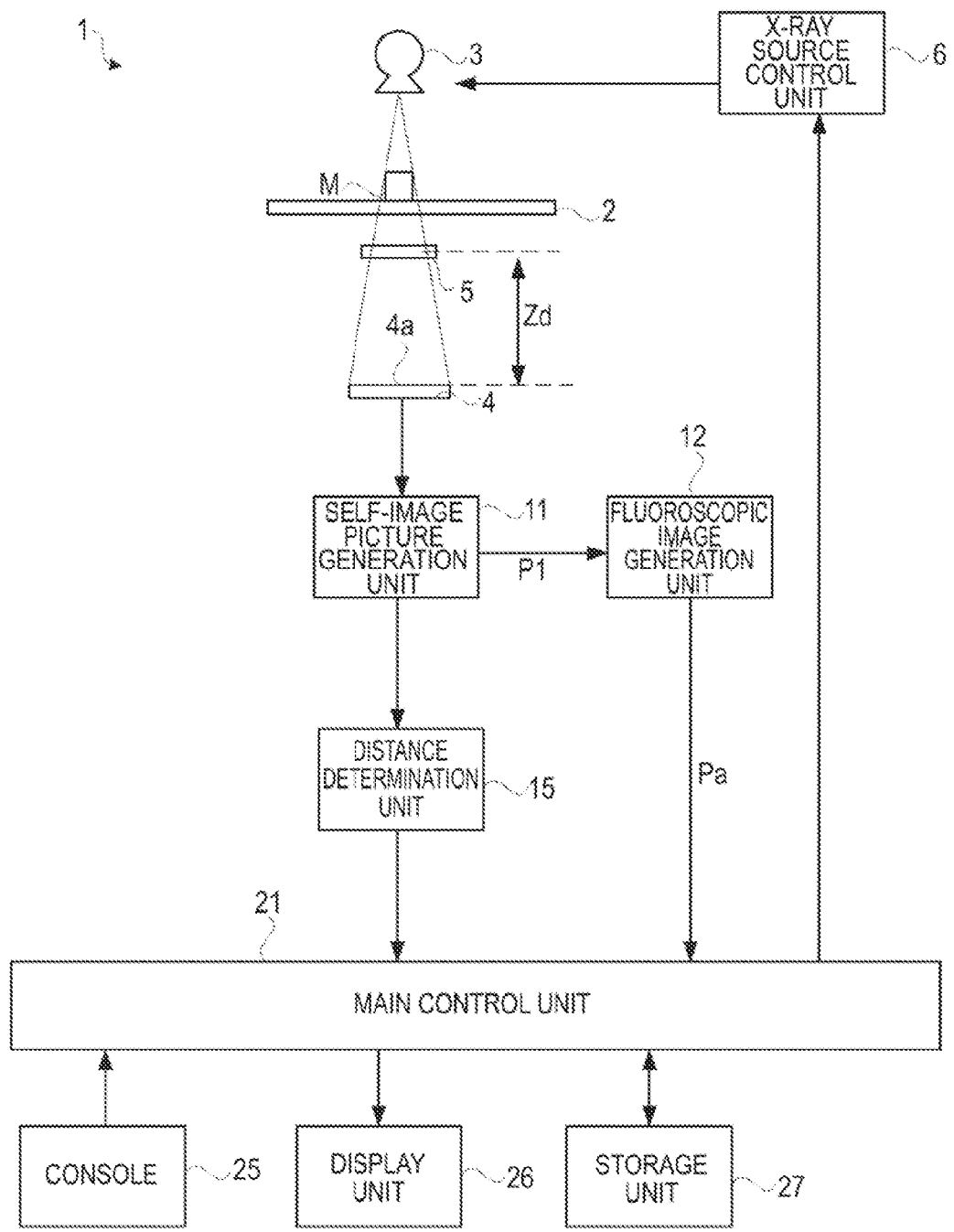
FIG. 1 is a functional block diagram showing an overall configuration of a radiation phase difference imaging apparatus according to a first embodiment.

The radiation phase difference imaging apparatus according to the invention will be described. FIG. 1 shows an overall configuration of an imaging apparatus 1 according to the invention. The imaging apparatus 1 includes, as shown in FIG. 1, a stage 2 on which the subject M is placed, the X-ray source 3 which is provided above the stage 2 and irradiates an X-ray beam spreading in a pyramidal shape, and the FPD 4 which detects the X-ray generated from the X-ray source 3 and transmitted through the subject M on the stage 2. The phase grating 5 which causes Talbot interference is provided at a position between the FPD 4 and the stage 2. The FPD 4 is configured to detect a self-image of the phase grating 5 generated by the Talbot interference using a detection surface 4a for detecting the X-ray. The X-ray source 3 corresponds to a radiation source of the invention and the FPD 4 corresponds to a detection unit of the invention.

The X-ray source 3 irradiates a plurality of kinds of X-rays having different wavelengths. That is, X-rays having relatively short and long wavelengths are included in the same X-rays among the X-rays output from the X-ray source 3. Thus, the X-ray source 3 does not radiate monochromatic X-rays. The shapes of the wavelength spectrums of the X-rays output from the X-ray source 3 are uniform.

The imaging apparatus 1 is a radiation imaging apparatus using the Talbot interference. Thus, the X-ray source 3 is configured to output an X-ray beam having the same phase. The self-image of the phase grating 5 appears on the detection surface for detecting the X-ray of the FPD 4. In a normal case, the distance between the phase grating 5 and the FPD 4 is set to a Talbot distance, but the invention is characterized in that the distance is determined from a different viewpoint not limited to such a common practice. In the configuration of the invention, it is difficult to strictly set the distance between the phase grating 5 and the FPD 4 to the Talbot distance. This is because the X-ray source 3 irradiates the X-rays having different wavelengths.

A self-image picture generation unit 11 generates the self-image of the phase grating 5 based on the output of the FPD 4. The generated self-image is output to a fluoroscopic image generation unit 12. The fluoroscopic image generation unit 12 generates a fluoroscopic image Pa obtained by imaging a phase difference of the X-ray generated by the subject M based on the self-image of the phase grating 5.

An X-ray source control unit 6 is provided for the purpose of controlling the X-ray source 3. During the imaging operation, the X-ray source control unit 6 controls the X-ray source 3 to output the X-ray beam in a pulse shape. When the X-ray source 3 outputs the X-ray beam, the FPD 4 detects the X-ray transmitted through the phase grating 5 and the subject M on the stage 3 and transmits detection data to the self-image picture generation unit 11. In this way, the apparatus of the invention is configured to generate the self-image by imaging the X-ray.

Figure 2:
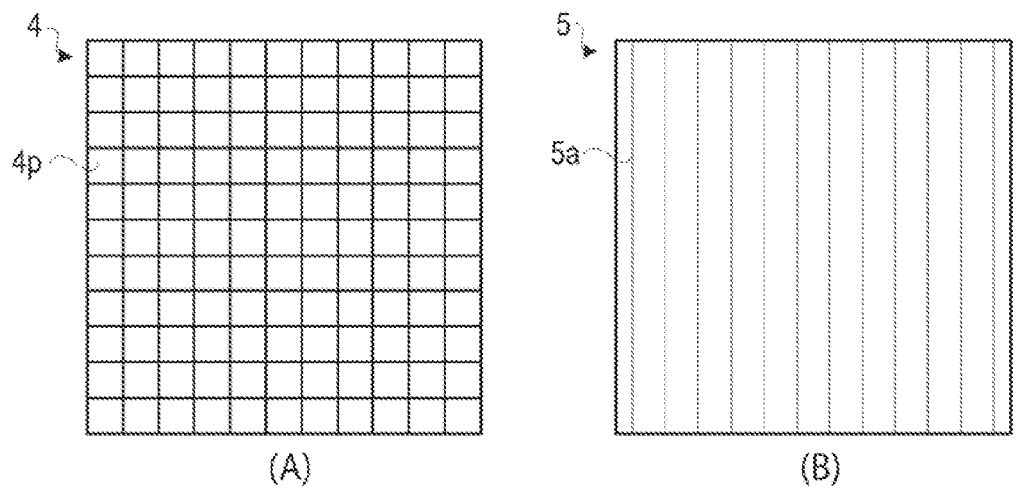
FIG. 2 is a top view showing a configuration of an FPD and a phase grating according to the first embodiment.

A left side of FIG. 2 illustrates the detection surface 4a of the FPD 4. On the detection surface 4a of the FPD 4, a detection element 4p having a rectangular shape of 20 μm in length×20 μm in width is arranged vertically and horizontally. The sizes of the detection element 4p and the detection surface 4a can be appropriately changed.

The FPD 4 is a direct conversion type X-ray detector. In other words, the FPD 4 has a conversion layer that converts X-rays into pairs of electrons and holes (pairs of carriers). The carriers which are generated at the conversion layers are respectively captured by the detection elements 4p to be accumulated. When a signal for outputting a carrier is transmitted to the detection element 4p, the detection element 4p outputs the accumulated carrier as a detection signal. The fineness of the detection element 4p is a main factor for determining the spatial resolution of the FPD 4. Since the spatial resolution of the FPD 4 becomes better as the detection element, 4p becomes smaller, a finer structure can be detected.

A right side of FIG. 2 illustrates the phase grating 5. The phase grating 5 has a structure in which the projection of the X-ray beam can be captured on the entire detection surface 4a of the FPD 4. Thus, the phase grating 5 has a rectangular structure as in the detection surface 4a of the FPD 4.

The phase grating 5 includes a plurality of absorption lines 5a which extend linearly to absorb the X-rays. The absorption lines 5a are arranged at a predetermined pitch in a direction orthogonal to the extension direction. The extension direction of the absorption line 5a of the phase grating 5 matches the vertical direction corresponding to the arrangement direction of the defection elements 4p of the detection surface 4a of the FPD 4 and the arrangement direction of the absorption lines 5a of the phase grating 5 matches the horizontal direction of the detection surface 4a of the FPD 4. In the phase grating 5, absorbers extending in one direction and absorbing X-rays are arranged in a direction orthogonal to one direction.

The FPD 4 transmits an X-ray detection signal to the self-image picture generation unit 11. The self-image picture generation unit 11 generates a self-image picture P1 capturing a self-image based on the transmitted detection signal. The self-image picture P1 is an image capturing the phase grating 5 as a whole. As shown in FIG. 1, the self-image picture P1 which is imaged while the subject M is set is captured such that the absorption line 5a of the phase grating 5 is distorted. This distortion represents an inner structure of the subject M due to a fact that the X-ray phase difference becomes uneven while the X-ray passes through the subject M.

The self-image picture P1 is transmitted to the fluoroscopic image generation unit 12. The fluoroscopic image generation unit 12 generates a fluoroscopic image Pa obtained by imaging a phase difference inside a subject based on the self-image picture P1 generated from the self-image picture generation unit 11.

The distance determination unit 15 is configured to determine the distance between the phase grating 5 and the FPD 4. The distance mentioned herein indicates a distance from the phase grating 5 to the detection surface 4a of the FPD 4. In the first embodiment, the distance determination unit 15 is mounted on the imaging apparatus 1, but the invention is not limited to this configuration. The distance determination unit 15 may be configured as a device independent from the imaging apparatus 1 and a positional relation between the phase grating 5 and the FPD 4 in the imaging apparatus 1 may be adjusted based on the output of the device.

Figure 3:
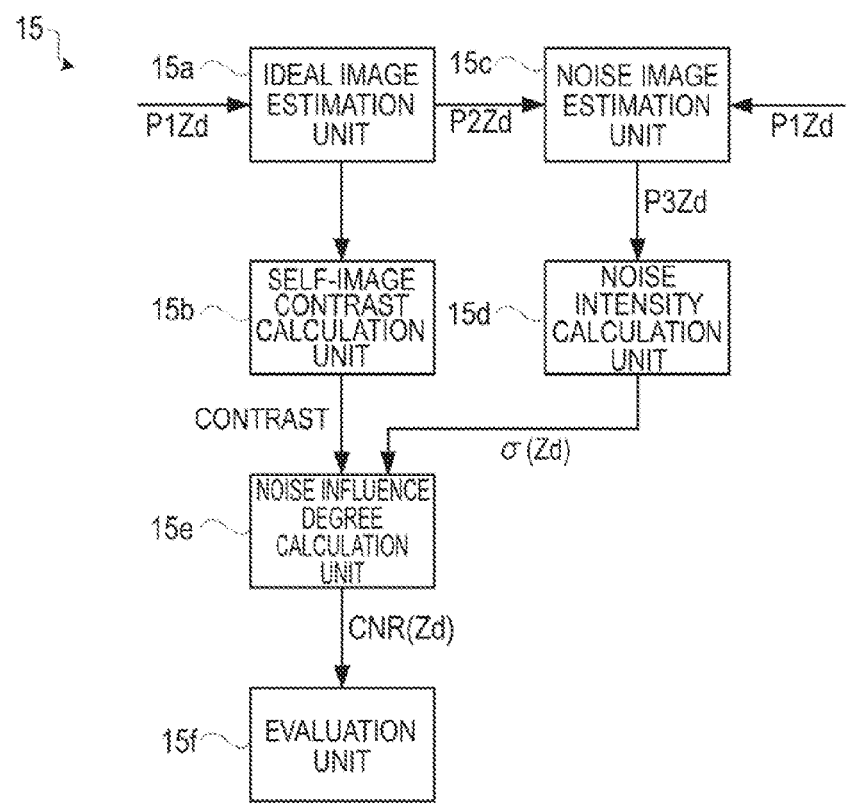
FIG. 3 is a functional block diagram showing a configuration of a distance determination unit according to the first embodiment.

FIG. 3 illustrates a configuration of the distance determination unit 15 that determines the distance between the phase grating 5 and the FPD 4. As shown in FIG. 3, the distance determination unit 15 is configured to estimate an ideal image picture P2Zd based on a measured self-image picture P1Zd, calculate a contrast of the self-image based on the ideal image picture P2Zd, estimate a noise component included in the self-image picture P1Zd based on the ideal image picture P2Zd to generate a noise image picture P3Zd, calculate a noise intensity of the self-image picture P1Zd based on the noise image picture P3Zd, calculate a noise influence degree representing a degree of the self-image disturbed by noise on the self-image picture based on the contrast I(Zd) max−I(Zd) min and the noise intensity σ(Zd), and evaluate whether the distance between the phase grating 5 and the FPD 4 at the time of obtaining the self-image picture P1Zd is suitable for imaging the self-image based on the noise influence degree. These operations are realized by an ideal image estimation unit 15a, a self-image contrast calculation unit 15b, a noise image estimation unit 15c, a noise intensity calculation unit 15d, a noise influence degree calculation unit 15e, and an evaluation unit 15f. The self-image contrast calculation unit 15b corresponds to an intensity calculation unit of the invention and the noise intensity calculation unit 15d corresponds to an intensity calculation unit of the invention.

<Method of Determining Distance Between Phase Grating 5 and FPD 4>

A method of determining the distance between the phase grating and the FPD 4 by the distance determination unit 15 will be conceptually described. It is considered that the distance between the phase grating 5 and the FPD 4 is an optimal distance based on the principle of the Talbot interference. However, when the configuration of the apparatus is considered, the optimal distance in the actual apparatus cannot foe calculated by a calculation based on the principle of the Talbot interference. This is because the distance is calculated on the assumption that the X-ray source 3 radiates only X-rays having a single wavelength in the calculation based on the principle of the Talbot interference. Since the x-ray source 3 of the invention is configured to irradiate a plurality of X-rays having different wavelengths, it is not guaranteed that the appropriate distance can be calculated for the imaging even when the calculation is performed while this fact is ignored.

Further, in an actual apparatus, since there are restrictions on the size of the whole apparatus, the size of the FPD 4, the size of the phase grating 5, and the arrangement of members, it is difficult to mention that the optimal distance can be realized in the apparatus. Thus, according to the configuration of the invention, it is configured to check whether a certain distance considered by an operator is acceptable for the purpose of imaging the self-image instead of calculating the optimal distance.

There is a need to prepare an appropriate reference for specifically checking whether the distance is suitable for imaging the self-image. Regarding this point, the configuration of the invention is contrived by focusing on the noise appearing in the self-image picture. When the distance between the phase grating 5 and the FPD 4 changes, the influence of the noise appearing in the self-image picture changes. Depending on the distance between the phase grating 5 and the FPD 4, the influence of the noise may increase or decrease. Focusing on this point, in the configuration of the invention, the noise influence degree appearing on the self-image picture at a certain distance is calculated and the suitability for the imaging of the self-image at the distance is checked based on the result. The distance between the phase grating 5 and the detection surface 4a of the FPD 4 is determined based on how much the self-image captured on the detection surface 4a is disturbed by noise.

In the invention, a value of the noise influence degree is considered as a value representing the noise influence degree. As the noise influence degree becomes smaller, the influence of the noise appearing in the self-image picture becomes larger. When the distance between the phase grating 5 and the FPD 4 changes, the noise influence degree also changes. Thus, the noise influence degree becomes the variable of the distance. The distance between the phase grating 5 and the FPD 4 is determined based on whether the noise influence degree representing how much the noise component appears on the self-image picture P1 guarantees the visibility of the fluoroscopic image Pa.

<CNR Calculation Method>

Figure 4:
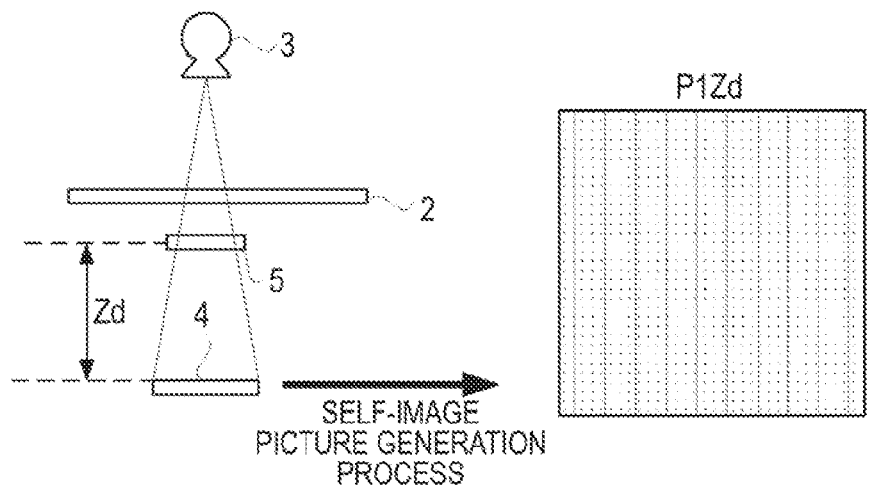
FIG. 4 is a schematic diagram showing a method of determining whether a distance between the phase grating and the FPD according to the first embodiment is suitable for imaging.

Next, as an example of a method of calculating the noise influence degree, a step of calculating the noise influence degree when the distance between the detection surface 4a of the FPD 4 and the phase grating 5 constituting the imaging apparatus 1 is Zd will be described. When the noise influence degree calculated at this time is sufficiently low, it is possible to mention that the distance Zd is suitable for imaging. In order to calculate the noise influence degree, the self-image is imaged by the imaging apparatus 1 in which the detection surface 4a of the FPD 4 is actually separated from the phase grating 5 by the distance Zd. FIG. 4 shows a state where the self-image picture P1Zd according to the distance Zd is generated by imaging. The self-image picture P1Zd is imaged while nothing is placed on the stage 2. Further, the self-image picture P1Zd may be imaged while the stage 2 is separated from the imaging apparatus 1. In the imaged self-image picture P1Zd, the self-image indicated by a vertical stripe in FIG. 4 and the noise indicated by shading are imaged at the same time. Since the self-image picture P1Zd is distinguished from the self-image picture P1 in which the subject M captured, attention is required.

Figure 5:
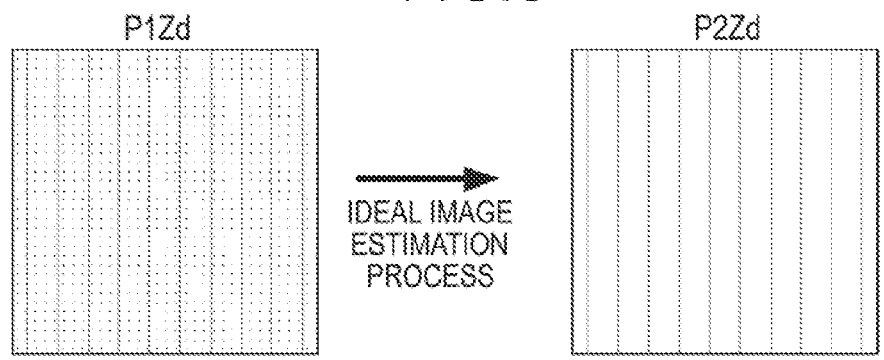
FIG. 5 is a schematic diagram showing a method of determining whether a distance between the phase grating and the FPD according to the first embodiment is suitable for imaging.

The generated self-image picture P1Zd is transmitted to the ideal image estimation unit 15a of the distance determination unit 15. As shown in FIG. 5, the ideal image estimation unit 15a generates the ideal image picture P2Zd by estimating the self-image captured on the self-image picture P1Zd. The ideal image picture P2Zd indicates the self-image obtained when no noise appears during the imaging of the self-image picture P1.

Figure 6:
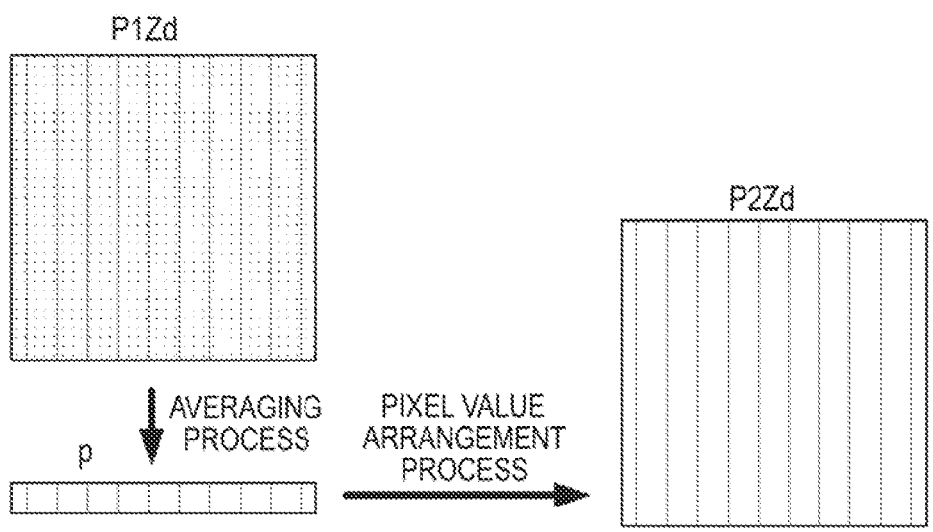
FIG. 6 is a schematic diagram showing a method of determining whether a distance between the phase grating and the FPD according to the first embodiment is suitable for imaging.

FIG. 6 more specifically shows the operation of the ideal image estimation unit 15a. The ideal image estimation unit 15a focuses on a column of pixels aligned in the vertical direction in the self-image picture P1Zd, acquires an average value of pixel values for each column, and calculates an average value corresponding to each pixel column as an array of pixel columns by arranging them horizontally in order to thereby generate an average value profile p. That is, the ideal image estimation unit 15a performs an averaging process on the pixel values in the direction in which the self-image striped pattern in the self-image picture P1Zd extends (the vertical direction in FIG. 6). The noise component superimposed on the self-image is cancelled by the averaging process and does not appear on the average value profile p. Meanwhile, the self-images formed by dark lines extending in the vertical direction have only average pixel values among pixels constituting the dark line by averaging process. Thus, the self-image appears on the average value profile p.

The ideal image estimation unit 15a generates the ideal image picture P2Zd by arranging the average value profile p in the vertical direction. In the generated ideal image picture P2Zd, the same number of pixels arranged in the self-image picture P1Zd are arranged vertically and horizontally. The ideal image picture P2Zd which is generated in this way becomes an image in which the stripe-shaped self-image is extracted from the self-image picture P1Zd.

The ideal image picture P2Zd is transmitted to the self-image contrast calculation unit 15b. The self-image contrast calculation unit 15b samples a pixel value I(Zd) max of pixels constituting bright lines of the ideal image picture P2Zd and a pixel value I(Zd) min of pixels constituting dark lines and calculates a contrast corresponding to a difference thereof. The contrast can be expressed by I(Zd) max−I(Zd) min. As a method of determining the pixel value I(Zd) max, a method of selecting the pixel value of the brightest pixel from the ideal image picture P2Zd is considered. Further, as a method of determining the pixel value I(Zd) min, a method of selecting the pixel value of the darkest pixel from the ideal image picture P2Zd is considered. The self-image contrast calculation unit 15b does not need calculate the contrast based on the ideal image picture P2Zd at all times. The ideal image estimation unit 15a can calculate the contrast based on the average value profile p generated among image processes.

Anyway, the self-image contrast calculation unit 15b calculates the contrast of the self-image captured on the self-image picture P1Zd when the phase grating 5 and the detection surface 4a are separated from each other by a certain distance Zd. The self-image contrast, calculation unit 15b calculates the contrast based on the measured self-image picture P1Zd.

Figure 7:
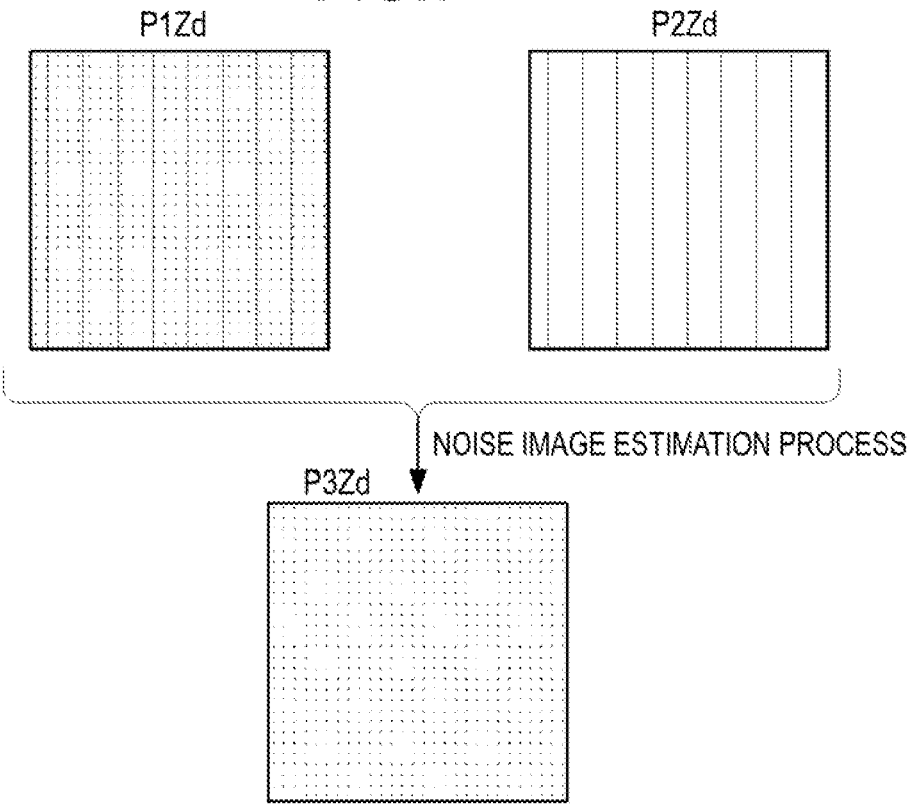
FIG. 7 is a schematic diagram showing a method of determining whether a distance between the phase grating and the FPD according to the first embodiment is suitable for imaging.

The ideal image picture P2Zd is also transmitted to the noise image estimation unit 15c. As shown in FIG. 7, the noise image estimation unit 15c subtracts the ideal image picture P2Zd from the self-image picture P1Zd to generate the noise image picture P3Zd in which only the noise component is captured on the self-image picture P1Zd. The noise image picture P3Zd becomes an image in which a sand storm-shaped noise component is extracted from the self-image picture P1Zd.

The noise image picture P3Zd is transmitted to the noise intensity calculation unit 15d. The noise intensity calculation unit 15d performs a statistical evaluation on the pixel value of the pixels constituting the noise image picture P3Zd to calculate the noise intensity σ(Zd) appearing on the noise image picture P3Zd. As indexes of the noise intensity, various indexes that statistically show variations in numerical values such as a full width at half maximum can be considered, but for example, the noise intensity σ(Zd) may be a variance of the pixel value. The noise intensity calculation unit 15d calculates the noise intensity σ(Zd) indicating the intensity of the noise component output from the FPD 4 at the time of generating the self-image picture P1 when the phase grating 5 and the detection surface 4a are separated from each other by a certain distance Zd. The noise intensity calculation unit 15d calculates the noise intensity σ(Zd) based on the measured self-image picture P1.

Figure 8:
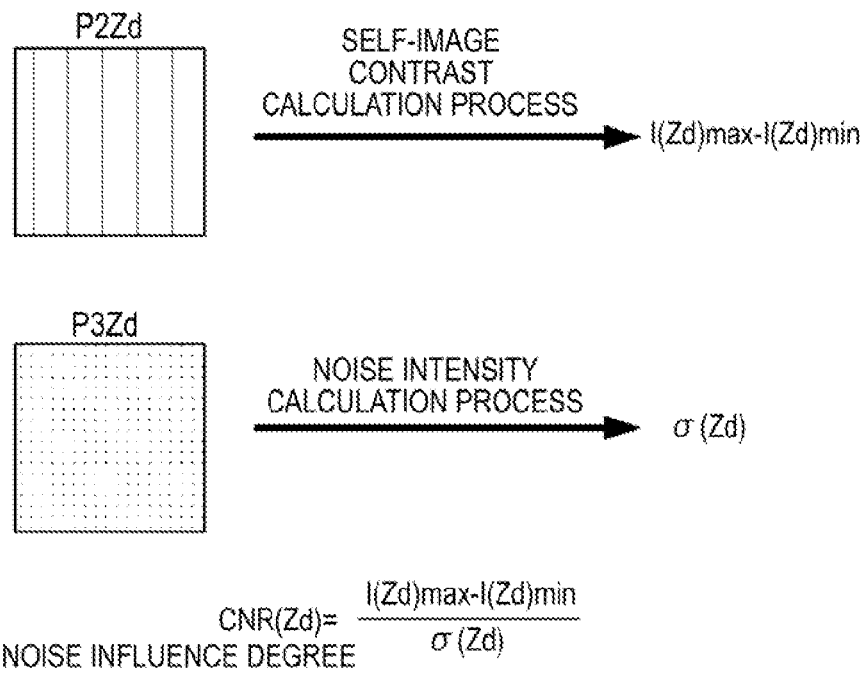
FIG. 8 is a schematic diagram showing a method of determining whether a distance between the phase grating and the FPD according to the first embodiment is suitable for imaging.

The contrast and the noise intensity σ(Zd) are transmitted to the noise influence degree calculation unit 15e. The noise influence degree calculation unit 15e divides the contrast by the noise intensity (Zd) to calculate the noise influence degree (CNR(Zd)). The noise influence degree is a concept similar to an S/N ratio and is an index indicating how much the self-image on the self-image picture P1Zd is disturbed by noise. FIG. 8 conceptually shows an operation of the self-image contrast calculation unit 15b, the noise intensity calculation unit 15d, and the noise influence degree calculation unit 15e. In this way, the noise influence degree calculation unit 15e calculates the noise influence degree (CNR(Zd))) based on the contrast and the noise intensity σ(Zd).

The noise influence degree is transmitted to the evaluation unit 15f. When the noise influence degree is equal to or smaller than the upper-limit value (reference value) stored in a storage unit 27, the evaluation unit 15f evaluates that the distance Zd is allowed as the distance from the phase grating 5 to the detection surface 4a of the FPD 4 for the purpose of imaging the self-image. Meanwhile, when the noise influence degree is larger than the upper-limit value, the evaluation unit 15f evaluates that the distance Zd is not allowed as the distance from the phase grating 5 to the detection surface 4a of the FPD 4 for the purpose of imaging the self-image. The operator can recognize whether the distance Zd is suitable for imaging based on the evaluation output from the evaluation unit 15f. The detection surface 4a of the FPD 4 may not be separated from the phase grating 5 by the distance which is evaluated not to be suitable. Otherwise, a clear self-image cannot be imaged. In this way, the evaluation unit 15f evaluates whether the distance Zd is a setting allowed for imaging the self-image based on the noise influence degree.

The upper-limit value which is stored in the storage unit 27 indicates the limit of the noise influence degree which is allowed at the time of imaging the self-image. When the noise influence degree is larger than the upper-limit value, the noise appearing on the self-image picture P1Zd becomes too strong and thus it can be determined that the self-image cannot be imaged. The upper-limit value can be determined based on the visibility of the fluoroscopic image Pa generated based on the self-image rather than the visibility of the self-image. The fluoroscopic image Pa is obtained by analyzing the stripe-shaped self-image and represents the inner structure of the subject.

As shown in FIG. 1, when the imaging is performed, while the subject M is set on the stage 2, the imaged self-image picture becomes an image in which the sand storm-shaped noise is superimposed on the stripe which is the self-image. When the fluoroscopic image Pa is generated based on such a self-image picture, the subject image on the fluoroscopic image is distorted by the influence of the noise on the self-image picture. In this way, the fluoroscopic image Pa is distorted by the noise on the self-image picture, but when the disturbance is too strong, the observation of the subject image on the fluoroscopic image is hindered.

The upper-limit value which is stored in the storage unit 27 indicates the noise influence degree of the self-image picture which is a base of the fluoroscopic image Pa which is considered to be invisible when the disturbance of the subject image becomes more. Thus, even when the fluoroscopic image Pa is generated based on the self-image picture in which the noise influence degree is larger than the upper-limit value, only the fluoroscopic image Pa having a problem in visibility is obtained. The self-image picture in which the noise influence degree is larger than the upper-limit value does not need to be imaged from the beginning. Such a self-image picture is imaged while the distance from the phase grating 5 to the detection surface 4a of the FPD 4 is not suitable.

According to the invention, when the upper-limit value of the noise influence degree of the self-image picture is set in advance, it is possible to prevent the generation of the fluoroscopic image Pa which is distorted to be invisible due to the unsuitable distance from the phase grating 5 to the detection surface 4a of the FPD 4.

As a method of determining the upper-limit value, when a sand storm-shaped noise component is synthesized with the self-image picture imaged while the subject is placed on the stage 2 to generate a synthesized image, the fluoroscopic image Pa generated based on the synthesized image is checked to obtain the upper-limit value. When a plurality of synthesized images are generated by switching the intensity of the noise component synthesized with the self-image picture and the fluoroscopic image Pa is generated based on these, the fluoroscopic image Pa with a strong noise component appears to the extent that the visibility is barely acceptable. The noise influence degree of the synthesized image based on the fluoroscopic image Pa is the upper-limit value. The noise influence degree at this time can be obtained from the contrast calculated from the self-image picture and the noise intensity calculated from the noise component. In addition, the noise component of the self-image picture to be synthesized is preferable as small as possible. Thus, the imaging of the self-image at the time of determining the upper-limit value may be performed with a long exposure time.

A main control unit 21 shown in FIG. 1 is provided for the purpose of integrally controlling the components 6, 11, 12, 14, and 15. The main control unit 21 is configured as a CPU and operates the components by performing various programs. Further, these components 6, 11, 12, 14, 15, 15a, 15b, 15c, 15d, 15e, and 15f may be separately operated by the calculation devices which are in charge of these components. These components can access to the storage unit 27 if necessary. A console 25 is provided for the purpose of inputting an instruction of the operator. Further, a display unit 26 is provided for the purpose of displaying a fluoroscopic image.

As described above, according to the invention, it is possible to reliably provide the X-ray phase difference imaging apparatus in which the separation distance between the phase grating 5 and the X-ray detector is optimized. Certainly, the separation distance between the phase grating 5 and the X-ray detector can be obtained as the Talbot distance based on the principle of the Talbot interference. However, the Talbot distance can be uniquely obtained only when the X-ray source 3 radiates a single wavelength.

Thus, according to the invention, the separation distance between the phase grating 5 and the detection surface 4a of the FPD 4 is determined based on how much the self-image captured on the detection surface 4a is disturbed by noise. That is, in the configuration of the invention, the noise influence degree is determined as an evaluation reference for the separation distance. Then, according to the invention, it is determined whether the distance 3d is suitable for imaging based on how much the self-image on the self-image picture obtained when the distance between the phase grating 5 and the detection surface 4a of the FPD 4 is set to a certain distance Zd is disturbed by noise. When it is determined that the distance Zd is suitable for imaging, the separation distance between the phase grating 5 and the detection surface 4a of the FPD 4 can be set to the distance Zd. Meanwhile, when it is determined that the distance Zd is not suitable for imaging, the determination on suitability is repeated while switching the separation distance. Likewise, a distance suitable for imaging can be found. In this way, it is possible to optimize the separation distance based on the actual condition of the actual X-ray source 3 radiating a plurality of kinds of X-rays.

The invention is not limited to the embodiment and can be modified as below.

(1) In the configuration of the embodiment, the noise influence degree is calculated by measuring the self-image picture P1, but the invention is not limited to this configuration. The noise influence degree can be calculated by a simulation. A method of obtaining the noise influence degree by the simulation will be described.

Even in the case of the simulation, the flow of estimating the noise intensity σ and the contrast of the self-image picture P1 and dividing these to obtain the noise influence degree does not change. Here, a method of obtaining the contrast of the self-image picture P1 will be first described.

Here, it is first assumed that the X-ray source 3 radiates X-rays having a single wavelength. At this time, it is possible to easily obtain a certain self-image in the detection surface 4a of the FPD 4 separated from the phase grating 5 by a predetermined distance Zd in terms of a simulation. In this assumption, the wavelength of the X-ray radiated by the X-ray source 3 is denoted by λa and the self-image appearing on the detection surface 4a of the FPD 4 at this time is denoted by $S(Zd)_{\lambda a}$. The self-image changes in response to a change in Zd. When λa is determined, the self-image $S(Zd)_{\lambda a}$ corresponding to an arbitrary distance Zd can be obtained by a simulation.

Meanwhile, when Zd is determined, a self-image $S(Zd)_{\lambda 1}$ corresponding to an arbitrary wavelength λ1 can be also obtained by a simulation. A plurality of self-images can be obtained by switching the wavelength λ. Here, the self-images $S(Zd)_{\lambda 1}$, $S(Zd)_{\lambda 2}$, $S(Zd)_{\lambda 3}$, . . . are calculated in the wavelengths λ1, λ2, λ3, . . . . These are simply referred to as $S_{\lambda 1}$, $S_{\lambda 2}$, $S_{\lambda 3}$, . . . .

The actual X-ray source 3 includes a plurality of radiations having different wavelengths λ1, λ2, λ3, . . . . When the self-image is imaged by using such an X-ray source 3, certain self-image $S(Zd)_{\lambda 1, \lambda 2, \lambda 3}$, . . . appear on the detection surface 4a of the FPD 4 separated from the phase grating 5 by a predetermined distance Zd. These are simply referred to as $S_{\lambda 1, \lambda 2, \lambda 3}$, . . . . The self-images can be expressed as below by the self-images $S_{\lambda 1}$, $S_{\lambda 2}$, $S_{\lambda 3}$, . . . obtained immediately before by a simulation.

$$S_{\lambda 1, \lambda 2, \lambda 3}, \ldots = k1 \cdot S_{\lambda 1} + k2 \cdot S_{\lambda 2} + k3 \cdot S_{\lambda 3} + \ldots$$

Here, k1, k2, k3, . . . are coefficients which are determined by how much the wavelengths λ1, λ2, λ3, . . . are output from the actual X-ray source 3. The coefficients can be easily obtained by the wavelength spectrum of the X-ray output from the X-ray source 3.

In this way, the self-images $S(Zd)_{\lambda 1, \lambda 2, \lambda 3}$, . . . can be obtained by a simulation. The self-images $S(Zd)_{\lambda 1, \lambda 2, \lambda 3}$, . . . are images corresponding to the ideal image picture P2Zd in the first embodiment and are estimated by the ideal image estimation unit 15a.

Subsequently, a method of obtaining the noise intensity σ(Zd) of the self-image picture P1 will be described. The method of obtaining the noise intensity σ(Zd) is actually similar to that of the self-images $S(Zd)_{\lambda 1, \lambda 2, \lambda 3}$, . . . .

That is, it is first assumed that the X-ray source 3 radiates X-rays having a single wavelength. At this time, it is possible to easily obtain a noise component in the detection surface 4a of the FPD 4 separated from the phase grating 5 by a predetermined distance Ed in terms of a simulation. On this assumption, the wavelength of the X-ray radiated from the X-ray source 3 is denoted by λa and the noise intensity occurring in the detection surface 4a of the FPD 4 at this time is denoted by $\sigma(Zd)_{\lambda a}$. The self-image changes in response to a change in Zd. When λa is determined, the noise intensity $\sigma(Zd)_{\lambda a}$ corresponding to an arbitrary distance Zd can be obtained by a simulation.

Meanwhile, when the value Zd is determined, a noise intensity $\sigma(Zd)_{\lambda 1}$ corresponding to an arbitrary wavelength λ1 can be also obtained by a simulation. A plurality of self-images can be obtained by switching the wavelength λ. Here, the noise intensities $\sigma(Zd)_{\lambda 1}$, $\sigma(Zd)_{\lambda 2}$, $\sigma(Zd)_{\lambda 3}$, . . . are calculated in the wavelengths λ1, λ2, λ3, . . . . These are simply referred to as $\sigma_{\lambda 1}$, $\sigma_{\lambda 2}$, $\sigma_{\lambda 3}$, . . . .

The actual X-ray source 3 includes a plurality of radiations having different wavelengths λ1, λ2, λ3, . . . . When the self-image is imaged by using such an X-ray source 3, certain noise intensities $\sigma(Zd)_{\lambda 1, \lambda 2, \lambda 3}$, . . . occur in the detection surface 4a of the FPD 4 separated from the phase grating 5 by a predetermined distance Zd. These are simply referred to as $\sigma_{\lambda 1, \lambda 2, \lambda 3}$, . . . . The self-images can be expressed as below by the noise intensities $\sigma_{\lambda 1}$, $\sigma_{\lambda 2}$, $\sigma_{\lambda 3}$, . . . obtained immediately before by a simulation.

$$\sigma_{\lambda 1, \lambda 2, \lambda 3}, \ldots = k1 \cdot \sigma_{\lambda 1} + k2 \cdot \sigma_{\lambda 2} + k3 \cdot \sigma_{\lambda 3} + \ldots$$

Here, k1, k2, k3, . . . are coefficients which are determined by the output degrees of the wavelengths λ1, λ2, λ3, . . . from the actual X-ray source 3. The coefficient can foe easily obtained by the wavelength spectrum of the X-ray output from the X-ray source 3.

In this way, the noise intensities $\sigma(Zd)_{\lambda 1, \lambda 2, \lambda 3}$, . . . can be calculated by a simulation. The noise intensities $\sigma(Zd)_{\lambda 1, \lambda 2, \lambda 3}$, . . . correspond to the noise intensities (Zd) of the first embodiment and are estimated by the noise intensity calculation unit 15d.

The operations of the self-image contrast calculation unit 15b, the noise influence degree calculation unit 15e, and the evaluation unit 15f of the modified example are similar to those of the first embodiment. In this way, the self-image contrast calculation unit 15b of the modified example calculates a contrast based on a simulation and the noise intensity calculation unit 15d calculates a noise intensity based on a simulation.

Figure 9:
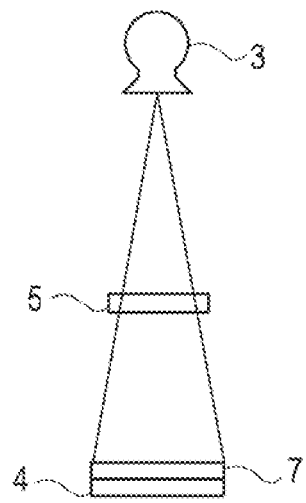
FIG. 9 is a schematic diagram showing one modified example of the invention.
Figure 10:
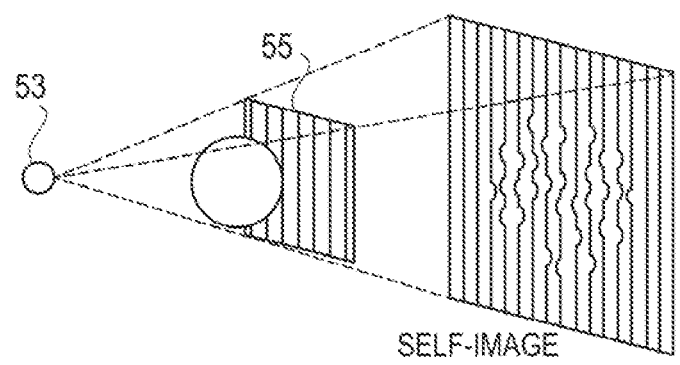
FIG. 10 is a schematic diagram showing a conventional apparatus configuration.

(2) In the configuration of the first embodiment, only the phase grating 5 is provided as the grating, but the invention is not limited to this configuration. As shown in FIG. 9, an absorption grating 7 may be provided to cover the detection surface 4a of the FPD 4. The absorption grating 7 has a configuration in which absorption lines are arranged similarly to the phase grating 5 and is provided for the purpose of generating moire by the interference with the self-image of the phase grating 5. The FPD 4 can estimate the self-image by detecting the moire. That is, the absorption grating 7 which generates moire with respect to the self-image of the phase grating 5 is provided between the phase grating 5 and the FPD 4 of the modified example.

(3) In the configuration of the first embodiment, the X-ray source 3 has a single focal point, but the invention is not limited to this configuration. The invention can be also applied to a configuration in which the X-ray source 3 includes a plurality of X-ray generation points.

INDUSTRIAL APPLICABILITY

As described above, the invention is suitable for a medical imaging apparatus.

REFERENCE SIGNS LIST 3 radiation source
4 FPD (detection unit)
4a detection surface
5 phase grating
7 absorption grating
P1 self-image picture
Pa fluoroscopic image
11 self-image picture generation unit
12 fluoroscopic image generation unit
15b self-image contrast calculation unit (intensity calculation unit)
15d noise intensity calculation unit (intensity calculation unit)
15e noise influence degree calculation unit (noise influence degree calculation unit)

The invention claimed is:

1. A radiation phase difference imaging apparatus comprising:
    a radiation source which radiates a plurality of radiations having different wavelengths;
    a phase grating in which absorbers extending in one direction and absorbing a radiation are arranged in a direction orthogonal to one direction;
    a detection unit which detects a self-image of the phase grating formed by a Talbot interference on a detection surface detecting a radiation;
    a self-image picture generation unit which generates a self-image picture capturing a self-image based on an output of the detection unit; and
    a fluoroscopic image generation unit which generates a fluoroscopic image obtained by imaging a phase difference inside a subject based on the self-image picture,
    wherein a distance between the phase grating and the detection surface of the detection unit is determined based on how much the self-image captured on the detection surface is disturbed by noise.

2. The radiation phase difference imaging apparatus according to claim 1, wherein the distance between the phase grating and the detection unit is determined by whether a noise influence degree representing how much the self-image picture is influenced by a noise component satisfies a reference for guaranteeing visibility of the fluoroscopic image.

3. The radiation phase difference imaging apparatus according to claim 1, wherein the distance between the phase grating and the detection surface is determined based on a noise influence degree calculated based on a contrast of a self-image captured on the self-image picture when the phase grating and the detection surface are separated from each other by a certain distance Zd and a noise intensity representing an intensity of a noise component reflected in the self-image picture.

4. The radiation phase difference imaging apparatus according to claim 3,
    wherein the noise influence degree is calculated by dividing the contrast by the noise intensity, and
    wherein it is evaluated that the distance Zd is allowed for imaging the self-image when the noise influence degree is equal to or smaller than a predetermined upper-limit value and it is evaluated that the distance Zd is not allowed for imaging the self-image when the noise influence degree is larger than the predetermined upper-limit value.

5. The radiation phase difference imaging apparatus according to claim 3,
    wherein the contrast and the noise intensity are calculated based on the measured self-image picture or a simulation.

* * * * *